(12) United States Patent
Lannibois-Drean et al.

(10) Patent No.: US 7,589,144 B2
(45) Date of Patent: *Sep. 15, 2009

(54) GRANULES OBTAINED BY DRYING A MULTIPLE EMULSION

(75) Inventors: Hélène Lannibois-Drean, Charenton le Pont (FR); Mikel Morvan, Princeton, NJ (US); Laurent Taisne, Paris (FR)

(73) Assignee: Rhodia Chimie, Cedex (FR)

( * ) Notice: Subject to any disclaimer, the term of this patent is extended or adjusted under 35 U.S.C. 154(b) by 277 days.

This patent is subject to a terminal disclaimer.

(21) Appl. No.: 11/490,339

(22) Filed: Jul. 20, 2006

(65) Prior Publication Data

US 2006/0258795 A1 Nov. 16, 2006

Related U.S. Application Data

(62) Division of application No. 10/399,653, filed on Aug. 11, 2003, now Pat. No. 7,101,931.

(30) Foreign Application Priority Data

Oct. 20, 2000 (FR) .................................... 00 13466

(51) Int. Cl.
*A61K 8/04* (2006.01)
*C08J 3/03* (2006.01)

(52) U.S. Cl. ....................... 524/501; 524/502; 524/503; 524/505; 524/801; 516/54; 516/56

(58) Field of Classification Search ................ 524/801, 524/501–505; 516/54, 56
See application file for complete search history.

(56) References Cited

U.S. PATENT DOCUMENTS

| 4,954,298 A | 9/1990 | Yamamoto ................... 264/4.6 |
| 5,750,124 A | 5/1998 | Gohla ......................... 424/401 |
| 5,840,943 A | 11/1998 | Ansmann ..................... 554/166 |
| 6,288,137 B1 * | 9/2001 | Iliopoulos et al. ........... 523/105 |
| 6,685,952 B1 | 2/2004 | Ma et al. |

OTHER PUBLICATIONS

"Ullmann's Encyclopedia of Industrial Chemistry, 5$^{th}$ Edition, vol. A9" 1988, VCH, Weinheim (Germany) XP00219246, p. 321-p. 325.

* cited by examiner

*Primary Examiner*—Irina S Zemel
(74) *Attorney, Agent, or Firm*—Hunton & Williams LLP

(57) ABSTRACT

The invention concerns granules obtainable by drying an inverse emulsion, dispersed in an external aqueous phase: a) the inverse emulsion comprising an internal aqueous phase, including a hydrophilic active material, dispersed in an internal organic phase, said inverse emulsion including at least a non-ionic surfactant and/or at least an amphiphilic block polymer, and/or at least a cationic surfactant; b) the external aqueous phase including: at least a polyalkylated non-ionic surfactant and/or at least a polalkylated amphiphilic non-ionic polymer; at least a water soluble or water dispersible polymer in solid form in the presence of a water content of not more than 10 wt. % relative to the weight of said polymer and whereof the glass transition temperature is higher than 25° C., preferably higher than 50° C. The granules, once dispersed, enable to obtain a multiple emulsion.

31 Claims, No Drawings

GRANULES OBTAINED BY DRYING A MULTIPLE EMULSION

This application is a division of U.S. application Ser. No. 10/399,653, filed on Aug. 11, 2003, now U.S. Pat. No. 7,101,931.

The subject of the present invention is granules which can be obtained by drying an inverse emulsion dispersed in an aqueous phase.

Multiple emulsions, or more particularly inverse emulsions (water-in-oil) dispersed in an aqueous phase are a very advantageous means, if desired, of introducing two incompatible hydrophilic active substances into the same formulation. The development of complex formulations, of the "two-in-one" type, means that these problems of incompatibility are increasingly encountered. It is indeed not rare to desire, during application, to have, in a mixture, two substances which, when they come into contact, react with each other. The use of multiple emulsions may also become essential when the formulation comprises several active substances which have to be kept apart because once in contact, one of them degrades the other, for example. Thus, in numerous instances, it is necessary to act so that the active substances come into contact only during the use of the formulation containing them, if it is not to be made ineffective and unusable.

Multiple emulsions may likewise provide an appropriate solution if, in a formulation comprising several active substances, it is desired to confer a delayed effect on one of them. Indeed, the active substance present in the inverse emulsion of the multiple emulsion will not be available as rapidly as that present in the aqueous external phase of the multiple emulsion.

The problem of multiple emulsions is that they are systems which are not in equilibrium, which means that they are relatively unstable. Means are known for remedying these problems of instability but they are only temporary. Indeed, while they provide a relatively satisfactory solution for conferring sufficient stability on this emulsion during the period for preparing the formulation containing it, they do not however make it possible to ensure the stability of the multiple emulsion during storage.

The subject of the present invention is therefore to provide a composition which is stable during storage, which is derived from a multiple emulsion and which can, if desired, be redispersed in an aqueous medium in the form of a multiple emulsion.

The invention therefore consists of granules which may be obtained by drying an inverse emulsion, dispersed in an external aqueous phase, (a) the inverse emulsion comprising an internal aqueous phase comprising at least one hydrophilic active substance, dispersed in an internal organic phase, said inverse emulsion comprising at least one nonionic surfactant and/or at least one amphiphilic block polymer and/or at least one cationic surfactant;

(b) the external aqueous phase comprising:
 at least one polyalkoxylated nonionic surfactant and/or at least one polyalkoxylated amphiphilic nonionic polymer,
 at least one water-soluble or water-dispersible polymer provided in a solid form in the presence of a water content of at most 10% by weight relative to the weight of said polymer and whose glass transition temperature is greater than 25° C., preferably greater than 50° C.

In the text which follows, the term "granules" denotes particles whose average size varies from 100 μm to a few millimeters.

As has been indicated above, the granules according to the invention have the advantage of being stable during storage and of giving again, after redispersion in an aqueous phase, a multiple emulsion.

It should be noted that it is quite surprising to observe that the drying operation, consisting in removing the external aqueous phase from the multiple emulsion, did not have the effect of completely removing water from the droplets of the inverse emulsion. Indeed, persons skilled in the art expected to have a phenomenon of destabilization of the multiple emulsion during the drying step, which would inevitably result in producing a simple emulsion after redispersing in an aqueous phase the granules obtained from the drying. However, contrary to what might have been expected, a multiple emulsion was again able to be obtained by dispersing in an aqueous medium granules obtained from drying such an emulsion.

Among other advantages of the granules obtained by drying a multiple emulsion, there may be mentioned that of being able to preserve an active substance in the form of an aqueous solution or dispersion, dispersed in a composition which has the appearance of a divided solid. Such granules make it possible to preserve substances requiring the presence of water to be active or which are active without an excessively long latent period. That is in particular the case for bacteria, enzymes or some hydrated salts.

However, other aims and advantages will appear more clearly on reading the description and the example which follow.

In the description, the term polymer denotes both homopolymers and copolymers.

Furthermore, the term macromonomer denotes a macromolecule carrying one or more functional groups capable of being polymerized, in particular by the free radical route.

For the sake of simplicity, in the disclosure of the invention, the inverse emulsion and its mode of preparation will first of all be detailed.

The inverse emulsion therefore consists of a water-in-oil emulsion. In the text which follows, the aqueous phase of this emulsion will be called internal aqueous phase, and the organic phase, the internal organic phase.

The compound used as organic phase is preferably chosen from compounds whose solubility in water does not exceed 10% by weight at 25° C.

In addition, said compound is chosen from those which are not removed under the conditions for drying the multiple emulsion.

As suitable compound, there may be mentioned in particular organic oils of animal or plant origin, or mineral oils, and waxes obtained from the same origins, or mixtures thereof.

As organic oils of animal origin, there may be mentioned, inter alia, cachalot oil, whale oil, seal oil, sardine oil, herring oil, shark oil, cod liver oil; lard, mutton fat (tallow).

As waxes of animal origin, beeswax may be mentioned.

As examples of organic oils of plant origin, there may be mentioned, inter alia, rapeseed oil, sunflower oil, peanut oil, olive oil, walnut oil, corn oil, soybean oil, linseed oil, hemp oil, grapeseed oil, copra oil, palm oil, cottonseed oil, babassu oil, jojoba oil, sesame oil, castor oil, cocoa butter, shea butter.

As waxes of plant origin, carnauba wax may be mentioned.

As regards the mineral oils, there may be mentioned, inter alia, petroleum fractions, naphthenic oils or paraffin oils (petroleum jelly). Paraffin waxes may likewise be suitable for preparing the emulsion.

The products derived from the alcoholysis of the abovementioned oils may also be used.

There would be no departure from the scope of the present invention by using, as internal organic phase, at least one saturated or unsaturated fatty acid, at least one saturated or unsaturated fatty alcohol, at least one fatty acid ester, or mixtures thereof.

More particularly, said acids comprise 8 to 40 carbon atoms, more particularly 10 to 40 carbon atoms, preferably 18 to 40 carbon atoms, and may comprise one or more conjugated or nonconjugated ethylenic unsaturations, and optionally one or more hydroxyl groups. As for the alcohols, they may comprise one or more hydroxyl groups.

As examples of saturated fatty acids, there may be mentioned palmitic, stearic and behenic acids.

As examples of unsaturated fatty acids, there may be mentioned myristoleic, palmitoleic, oleic, erucic, linoleic, linolenic, arachidonic and ricinoleic acids, and mixtures thereof.

As for the alcohols, these comprise more particularly 4 to 40 carbon atoms, preferably 10 to 40 carbon atoms, optionally one or more conjugated or nonconjugated ethylenic unsaturations, and optionally several hydroxyl groups. The polymers comprising several hydroxyl groups may likewise be suitable, such as for example polypropylene glycols.

As an example of alcohols, there may be mentioned, for example, those corresponding to the abovementioned acids.

As regards the fatty acid esters, these may advantageously be obtained from fatty acids, chosen from the compounds named above. The alcohols from which these esters are prepared comprise more particularly 1 to 6 carbon atoms. Preferably, they are methyl, ethyl, propyl and isopropyl esters.

Moreover, using mono-, di- and triglycerides as organic phase is not excluded.

Finally, the organic phase may comprise a quantity of water which does not exceed the limit of solubility of water in said organic phase (at a temperature between 20 and 30° C.).

The internal organic phase may likewise be chosen from alkyd resins (such as for example the resins Coporob 3115 DE, marketed by the company Novance), epoxy resins, (poly) isocyanates which are masked or unmasked.

It may also be chosen from essential oils and silicone oils.

The internal organic phase may comprise at least one hydrophobic active substance, provided that it is compatible with the hydrophilic active substance present in the internal aqueous phase, which will be described in the text which follows.

Said active substances are in a liquid or nonliquid form which is soluble in the organic phase or solubilized in an organic solvent miscible with the organic phase, or in the form of a solid in dispersion in said phase.

In the case where an organic solvent is present, it is preferably chosen from the substances which are not removed under the conditions for drying the emulsion.

More particularly, the active substances are such that their solubility in water does not exceed 10% by weight at 25° C.

In addition, the active substances preferably have a melting point of less than or equal to 100° C., more particularly less than or equal to 80° C.

It is likewise specified that the organic active substances are advantageously chosen from the compounds which are not removed under the conditions for drying the multiple emulsion.

By way of example of active substances in the food sector, there may be mentioned mono-, di- and triglycerides, essential oils, flavorings and colorings.

By way of example of active substances in the cosmetic field, there may be mentioned silicone oils belonging, for example, to the family of dimethicones; lipophilic vitamins, such as vitamin A.

By way of example of active substances suitable for carrying out the invention, in the paints sector, there may be mentioned alkyd resin, epoxy resins, (poly)isocyanates which are masked or unmasked.

In the paper sector, there may be mentioned, by way of example, bonding and water-repellant resins such as the alkylketene dimer (AKD) or alkenylsuccinic anhydride (ASA).

In the agrochemical field, the plant-protection active substances may be chosen from the family of α-cyanophenoxybenzylcarboxylates or of α-cyanohalophenoxycarboxylates, the family of N-methylcarbonates comprising aromatic substituents, active substances such as Aldrin, Azinphos-methyl, Benfluralin, Bifenthrin, Chlorphoxim, Chlorpyrifos, Fluchloralin, Fluroxypyr, Dichlorvos, Malathion, Molinate, Parathion, Permethrin, Profenofos, Propiconazole, Prothiofos, Pyrifenox, Butachlor, Metolachlor, Chlorimephos, Diazinon, Fluazifop-P-butyl, Heptopargil, Mecarbam, Propargite, Prosulfocarb, Bromophos-ethyl, Carbophenothion, Cyhalothrin.

In the detergency domain, silicone antifoams may be mentioned as possible active substances.

It is likewise possible to use active substances such as those entering into the composition of lubricants for working or deforming materials. The active substance is usually an oil, a derivative of an oil or alternatively a fatty acid ester.

The active substance may be chosen from organic solvents or mixtures of such solvents which are sparingly miscible or immiscible in water, such as in particular those used for cleaning or stripping, such as aromatic petroleum cuts, terpenic compounds such as D- or L-limonenes, and solvents such as Solvesso®. Also suitable as solvents are aliphatic esters, such as the methyl esters of a mixture of acetic, succinic and glutaric acids (mixture of acids which is a by-product of the synthesis of Nylon), hydrocarbon oils such as liquid paraffin, and chlorinated solvents.

In the case where the internal organic phase comprises one or more different hydrophobic active substances of the organic phase, their content represents more particularly 10 to 50% by weight of said internal organic phase.

Finally, the organic phase itself may be considered as a hydrophobic active substance.

The inverse emulsion comprises, in addition, at least one nonionic surfactant and/or at least one amphiphilic block polymer, and/or at least one cationic surfactant.

According to a first variant, the inverse emulsion comprises at least one nonionic surfactant or at least one amphiphilic block polymer, or a mixture thereof.

It should be noted that the Bancroft rule may be applied to the nonionic surfactant and to the amphiphilic block polymer used (2nd World Conference on Emulsion, 1997, Bordeaux, France). In other words, the fraction soluble in the continuous phase is greater than the fraction soluble in the dispersed phase.

Thus, the surfactant and the polymer are preferably chosen from those which satisfy both of the two conditions below:

when they are mixed with the internal organic phase, at a concentration between 0.1 and 10% by weight of said phase at 25° C., they are in the form of a solution in the whole or part of the concentration range indicated;

when they are mixed with the internal aqueous phase, at a concentration between 0.1 and 10% by weight of said phase and at 25° C., they are in the form of a dispersion in the whole or part of the concentration range indicated.

More particularly, the nonionic surfactant is chosen from compounds having an HLB (hydrophilic/lipophilic balance) value of less than or equal to 8.

By way of examples of surfactants which may enter into the composition of the inverse emulsion, there may be mentioned surfactants, alone or in the form of a mixture, chosen from:
alkoxylated fatty alcohols
alkoxylated triglycerides
alkoxylated fatty acids
optionally alkoxylated sorbitan esters
alkoxylated fatty amines
alkoxylated di(1-phenylethyl)phenols
alkoxylated tri(1-phenylethyl)phenols
alkoxylated alkylphenols the number of alkoxylated (ethoxylated, propoxylated, butoxylated) units is such that the HLB value is less than or equal to 8.

The alkoxylated fatty alcohols generally comprise from 6 to 22 carbon atoms, the alkoxylated units being excluded from these numbers.

The alkoxylated triglycerides may be triglycerides of plant or animal origin.

The optionally alkoxylated sorbitan esters are cyclized sorbitol esters of fatty acids comprising from 10 to 20 carbon atoms, such as lauric acid, stearic acid or oleic acid.

The alkoxylated fatty amines generally have from 10 to 22 carbon atoms, the alkoxylated units being excluded from these numbers.

The alkoxylated alkylphenols generally have one or two linear or branched alkyl groups having 4 to 12 carbon atoms. By way of example, there may be mentioned in particular octyl, nonyl or dodecyl groups.

As for the amphiphilic block polymer, it comprises at least two blocks.

These amphiphilic polymers, which satisfy the Bancroft rule and the two conditions set out above, comprise more particularly at least one hydrophobic block and at least one neutral, anionic or cationic hydrophilic block.

In the case where the amphiphilic polymer comprises at least three blocks, and more particularly three blocks, the polymer is preferably linear. In addition, the hydrophobic blocks are more particularly at the ends.

In the case where the polymers comprise more than three blocks, the latter are preferably in the form of graft or comb polymers.

In the text which follows, even though this constitutes a misuse of language, the term amphiphilic block polymer will be used without distinction for linear block polymers and graft or comb polymers.

Said amphiphilic polymers may advantageously be obtained by the so-called live or controlled free-radical polymerization. By way of nonlimiting examples of methods of so-called live or controlled polymerization, reference may be made in particular to applications WO 98/58974 (xanthate), WO 97/01478 (dithioesters), WO 99/03894 (nitroxides); WO 99/31144 (dithiocarbamates).

The amphiphilic polymers may also be obtained by cationic or anionic polymerization.

They may likewise be prepared using (in particular anionic or cationic) ring opening polymerizations, or by chemical modification of the polymer.

The graft of comb polymers may also be obtained by so-called direct grafting and copolymerization methods.

Direct grafting consists in polymerizing the chosen monomer(s) by the free-radical route, in the presence of the selected polymer to form the backbone of the final product. If the monomer/backbone pair and the operating conditions are judiciously chosen, then a transfer reaction may take place between the growing macroradical and the backbone. This reaction generates a radical on the backbone, and it is from this radical that the graft grows. The primary radical obtained from the initiator may also contribute to the transfer reactions.

As regards the copolymerization, it uses, in a first instance, grafting to the end of the future pendent segment a functional group which can be polymerized by the free-radical route. This grafting may be carried out by customary methods of organic chemistry. Next, in a second instance, the macromonomer thus obtained is polymerized with the chosen monomer to form the backbone and a so-called "comb" polymer is obtained.

Among the hydrophobic monomers from which the hydrophobic blocks of the amphiphilic polymer may be prepared, there may be mentioned in particular:
esters of linear, branched, cyclic or aromatic, mono- or polycarboxylic acids comprising at least one ethylenic unsaturation,
esters of saturated carboxylic acids comprising 8 to 30 carbon atoms, optionally carrying a hydroxyl group;
$\alpha\beta$-ethylenically unsaturated nitriles, vinyl ethers, vinyl esters, vinylaromatic monomers, vinyl or vinylidene halides,
linear or branched, aromatic or nonaromatic hydrocarbon monomers comprising at least one ethylenic unsaturation,
monomers of the cyclic or noncyclic siloxane type, chlorosilanes;
propylene oxide, butylene oxide;

alone or in the form of mixtures, and macromonomers derived from such monomers.

By way of particular examples of hydrophobic monomers which may enter into the preparation of the hydrophobic block(s) of the amphiphilic block polymer, there may be mentioned:
esters of (meth)acrylic acid with an alcohol comprising 1 to 12 carbon atoms such as methyl (meth)acrylate, ethyl (meth)acrylate, propyl (meth)acrylate, n-butyl (meth) acrylate, t-butyl (meth)acrylate, isobutyl (meth)acrylate, 2-ethylhexyl acrylate;
vinyl acetate, vinyl Versatate®, vinyl propionate, vinyl chloride, vinylidene chloride, methyl vinyl ether, ethyl vinyl ether;
the vinyl nitriles include more particularly those having from 3 to 12 carbon atoms, such as in particular acrylonitrile and methacrylonitrile;
styrene, $\alpha$-methylstyrene, vinyltoluene, butadiene, chloroprene;

alone or in the form of mixtures, and the macromonomers derived from such monomers.

The preferred monomers are esters of acrylic acid with linear or branched $C_1$-$C_4$ alcohols such as methyl, ethyl, propyl and butyl acrylate, vinyl esters such as vinyl acetate, styrene, $\alpha$-methylstyrene.

As regards the nonionic hydrophilic monomers from which the amphiphilic block polymers may be obtained, there may be mentioned, with no limitation being implied, ethylene oxide, amides of linear, branched, cyclic or aromatic mono- or polycarboxylic acids comprising at least one ethylenic unsaturation or derivatives, such as (meth)acrylamide, N-methylol (meth)acrylamide; hydrophilic esters derived from (meth)acrylic acid such as for example 2-hydroxyethyl (meth)acrylate; vinyl esters which make it possible to obtain polyvinyl alcohol blocks after hydrolysis, such as vinyl acetate, vinyl Versatate®, vinyl propionate, alone or in combination, and macromonomers derived from such monomers. It is recalled that the term macromonomer denotes a macromolecule carrying one or more polymerizable functional groups.

However, the preferred hydrophilic monomers are acrylamide and methacrylamide, alone or in the form of a mixture, in the form of macromonomers.

As regards the anionic hydrophilic monomers from which the amphiphilic block polymers may be obtained, there may be mentioned, for example, monomers comprising at least one carboxylic, sulfonic, sulfuric, phosphonic, phosphoric, or sulfosuccinic functional group, or the corresponding salts.

It is specified that under the pH conditions for using the amphiphilic block polymer, the functional groups of the anionic block(s) of the polymer are in a form which is at least partially ionized (dissociated). More particularly, at least 10 mol % of the functional groups of the block(s) are in ionized form. The determination of this volume does not pose any problem for persons skilled in the art; it depends in particular on the pKa of the ionizable functional groups of the units of the polymer and on the number of these functional groups (that is on the number of mol of monomer carrying ionizable functional groups used during the preparation of the polymer).

More particularly, the monomers are chosen from:
linear, branched, cyclic or aromatic mono- or polycarboxylic acids, N-substituted derivatives of such acids; monoesters of polycarboxylic acids, comprising at least one ethylenic unsaturation;
linear, branched, cyclic or aromatic vinylcarboxylic acids;
amino acids comprising one or more ethylenic unsaturations;

alone or in the form of mixtures, their precursors, their sulfonic or phosphonic derivatives, and the macromonomers derived from such monomers; it being possible for the monomers or macromonomers to be in the form of salts.

By way of examples of anionic monomers, there may be mentioned without limitation being implied:
acrylic acid, methacrylic acid, fumaric acid, itaconic acid, citraconic acid, maleic acid, acrylamido glycolic acid, 2-propene-1-sulfonic acid, methallylsulfonic acid, styrenesulfonic acid, α-acrylamidomethylpropanesulfonic acid, 2-sulfoethylene methacrylate, sulfopropylacrylic acid, bis-sulfopropylacrylic acid, bis-sulfopropylmethacrylic acid, sulfatoethylmethacrylic acid, phosphate monoester of hydroxyethyl methacrylic acid, and the alkali metal salts, such as sodium or potassium, or ammonium salts;
vinylsulfonic acid, vinylbenzenesulfonic acid, vinylphosphonic acid, vinylidenephosphoric acid, vinylbenzoic acid, and the alkali metal salts, such as sodium or potassium, or ammonium salts;
N-methacryloylalanine, N-acryloylhydroxyglycine;

alone or in the form of mixtures, and the macromonomers derived from such monomers.

There would be no departure from the scope of the present invention in using monomers which are precursors of those which have just been cited. In other words, these monomers have units which, once incorporated into the polymer chain, may be converted, in particular by chemical treatment such as hydrolysis, to give again the abovementioned anionic species. For example, the completely or partially esterified monomers of the abovementioned monomers may be used so as to be subsequently completely or partially hydrolyzed.

As hydrophilic cationic monomers from which the amphiphilic block polymers may be obtained, there may be mentioned in particular:
aminoalkyl (meth)acrylates, aminoalkyl (meth)acrylamides;
monomers comprising at least one secondary, tertiary or quaternary amine functional group, or a heterocyclic group containing a nitrogen atom, vinylamine, ethyleneimine;
ammonium salts of diallyldialkyl;

alone or in the form of mixtures, or the corresponding salts and the macromonomers derived from such monomers.

Said monomers may be provided as a counter-ion chosen from halides such as, for example, chlorine, sulfates, hydrosulfates, alkyl sulfates (for example comprising 1 to 6 carbon atoms), phosphates, citrates, formates, acetates.

By way of examples of suitable cationic monomers are, inter alia, the following monomers:
dimethylaminoethyl (meth)acrylate, dimethylaminopropyl (meth)acrylate, di-tert-butylaminoethyl (meth)acrylate, dimethylaminomethyl (meth)acrylamide, dimethylaminopropyl (meth)acrylamide;
ethyleneimine, vinylamine, 2-vinylpyridine, 4-vinylpyridine;
trimethylammonium ethyl (meth)acrylate chloride, trimethylammonium ethyl acrylate methyl sulfate, benzyl dimethylammonium ethyl (meth)acrylate chloride, 4-benzoylbenzyldimethylammonium ethyl acrylate chloride, trimethylammonium ethyl (meth)acrylamido chloride, vinylbenzene trimethylammonium chloride;
diallyldimethyl ammonium chloride;

alone or in the form of mixtures, or their corresponding salts, and the macromonomers derived from such monomers.

Preferably, the amphiphilic block polymers have a weight-average molar mass of less than or equal to 100 000 g/mol, more particularly between 1 000 and 50 000 g/mol, preferably between 1 000 and 20 000 g/mol. It is specified that the weight-average molar masses indicated above are theoretical molar masses evaluated according to the respective quantities of the monomers introduced during the preparation of said polymers.

Preferably, an amphiphilic block polymer of the nonionic type is used.

By way of example of an amphiphilic block polymer suitable for carrying out the invention, there may be mentioned polyhydroxystearate-polyethylene glycol-polyhydroxystearate triblock polymers (the products in the Arlacel range from ICI are an example thereof), polyether polyalkyl graft polydimethylsiloxane block polymers (such as the products of the trademark Tegopren marketed by Goldschmidt).

According to a second variant, the inverse emulsion comprises at least one cationic surfactant.

In the case of this variant, it is indicated that the cationic surfactant does not satisfy the Bancroft rule set out above. Indeed, the cationic surfactant is soluble in a dispersed phase and not in the continuous phase of the inverse emulsion.

Among the suitable cationic surfactants, there may be used in particular aliphatic or aromatic fatty amines, aliphatic fatty amides, quaternary ammonium derivatives (Rhodaquat RP50 from Rhodia Chimie).

Finally, a third variant of the invention consists in combining the two possibilities which have just been detailed.

Regardless of the variant selected, the total content of nonionic surfactant, of amphiphilic block polymer and/or of cationic surfactant, represents more particularly from 0.1 to 10% by weight, preferably from 2 to 10% by weight relative to the internal aqueous phase.

The internal aqueous phase comprises at least one hydrophilic active substance, provided in a form soluble in the internal aqueous phase; in a form solubilized in a water-miscible solvent such as methanol, ethanol, propylene glycol, glycerol; in the form of a solid dispersed in said phase.

The quantity of hydrophilic active substance, if it is present, is in a content which is more particularly between 0.1 and 50% by weight of the internal aqueous phase, and preferably between 0.1 and 20% by weight of the internal aqueous phase.

Given the large number of fields in which the granules according to the invention may be used, many active substances may be suitable for implementing the invention.

By way of example of active substances which may be used in the cosmetic field, there may be mentioned substances which have a cosmetic effect, a therapeutic effect or any other substance which may be used for treating the skin and the hair.

Accordingly, it is possible to use, as active substance, conditioning agents for the skin and the hair, such as in particular polymers comprising quaternary ammoniums which may be optionally used in heterocycles (compounds of the quaternium and polyquaternium types, and the like), humectants; fixing (styling) agents which are more particularly chosen from polymers (homo-, co- or terpolymers, for example acrylamide, acrylamide/sodium acrylate, polystyrene sulfonate, and the like), cationic polymers, polyvinylpyrrolidone, polyvinyl acetate, and the like.

It is likewise possible to use colorants; astringents, which can be used in deodorants and which are more particularly aluminum or zirconium salts; antibacterial agents; anti-inflammatory agents, anesthetizing agents, sunscreens, and the like.

There may also be mentioned $\alpha$- and $\beta$-hydroxy acids, such as citric, lactic, glycolic and salicylic acids; dicarboxylic acids, preferably unsaturated and comprising 9 to 16 carbon atoms such as azelaic acid; vitamin C and its derivatives, in particular the glycosylated and phosphated derivatives; biocides, in particular cationic biocides (Glokill PQ, Rhodoaquat RP50, marketed by Rhodia Chimie), as active substances suitable in cosmetic formulations.

In the food sector, there may be mentioned, for example, divalent calcium salts (phosphates, chlorides, and the like) which are used as crosslinking agent for texturing polymers such as alginates, carrageenans; sodium bicarbonate, among others.

In the field of plant-protection active substances, it is possible to use hydrophilic pesticides or hydrophilic nutritive components which promote the growth and development of plants.

As regards the field for the exploitation or construction of oil or gas wells, the present invention may be used for hydrophilic active substances which may be used in particular during operations of cementation, completion, drilling and stimulation of wells (for example fracturing). By way of examples of active substances which can be used in this field, there may be mentioned catalysts for crosslinking of cement-based compositions, such as for example lithium salts, such as the chloride and acetate. There may even be mentioned compounds which are capable, inter alia, of degrading polysaccharides, such as for example carboxylic acids (in particular citric acid), enzymes (in particular cellulases), oxidants.

In the field of silicones, there may be mentioned, for example, calcium salts, potassium hydroxide, which are normally used as crosslinking agents.

By way of active substances which are suitable in the papermaking field, calcium chloride and hydrochloric acid may in particular be mentioned.

In accordance with a particularly advantageous embodiment of the present invention, the internal aqueous phase may comprise at least one additive chosen from salts such as alkali or alkaline-earth metal halides (such as sodium chloride and calcium chloride), or alkali or alkaline-earth metal sulfates (such as calcium sulfate), or mixtures thereof. The internal aqueous phase may also comprise, as additive, at least one sugar, such as glucose for example, or alternatively at least one polysaccharide, such as in particular dextran, or mixtures thereof.

The concentration of salt in the internal aqueous phase, when the latter is present, is more particularly between 0.05 and 1 mol/l, preferably 0.1 to 0.4 mol/l.

The concentration of sugar and/or polysaccharide is such that the osmotic pressure of the internal aqueous phase comprising the sugar and/or the polysaccharide corresponds to the osmotic pressure of an internal aqueous phase comprising 0.05 to 1 mol/l of salt.

In addition, the inverse emulsion has more particularly an internal aqueous phase/internal organic phase weight ratio between 10/90 and 90/10. Preferably, the aqueous phase/organic phase weight ratio is between 30/70 and 80/20.

The inverse emulsion is prepared using conventional methods.

Thus, to cite only one, there are prepared, on the one hand, a first mixture comprising water, the hydrophilic active substance, the cationic surfactant if it is present, and optionally the additive (salt, sugar and/or polysaccharide) and, on the other hand, a second mixture comprising the compound constituting the internal organic phase, optionally the hydrophobic active substance, and the surfactant and/or the amphiphilic block polymer, if they are present. The first mixture is then mixed with the second, with stirring.

In the case where the organic phase is not very viscous (viscosity less than 5 Pa·s; dynamic viscosity measured using Brookfield at 25° C., according to the NFT 76 102 standard of February 1972), the stirring is preferably vigorous and may advantageously be provided using an apparatus such as Ultra-Turrax®, Microfluidizer, or any high-pressure homogenizer.

In the case where the organic phase is viscous (viscosity greater than or equal to 5 Pa·s, measured as above), the stirring may be advantageously carried out by means of a frame-type blade.

The preparation of the inverse emulsion is generally carried out at a temperature greater than the melting point of the compound constituting the internal organic phase. More particularly, the temperature for preparing the inverse emulsion is between 20 and 80° C.

The duration of the stirring may be determined without difficulty by persons skilled in the art and depends on the type of apparatus used. It is preferably sufficient to obtain a mean droplet size of between 0.1 and 10 µm, preferably between 0.1 and 5 µm (measured by means of a Horiba granulometer). It is recalled that the mean size of the droplets is measured using a Horiba granulometer, and corresponds to the median diameter by volume (d50) which represents the diameter of the particle equal to 50% of the cumulative distribution.

The aqueous external phase of the multiple emulsion will now be described.

The external aqueous phase comprises at least one nonionic polyalkoxylated surfactant and/or at least one nonionic polyalkoxylated amphiphilic polymer, and at least one water-soluble or water-dispersible compound.

Here again, the Bancroft rule may be applied to the surfactant and to the polymer used. In other words, the fraction soluble in the continuous phase is higher than the fraction soluble in the dispersed phase.

The surfactant and the polymer therefore simultaneously satisfy both of the two conditions mentioned below:
- when they are mixed with the external aqueous phase, at a concentration of between 0.1 and 10% by weight of said phase at 25° C., they exist in the form of a solution in the whole or part of the concentration range indicated;
- when they are mixed with the internal organic phase, at a concentration between 0.1 and 10% by weight of said phase and at 25° C., they exist in the form of a dispersion in the whole or part of the concentration range indicated.

Preferably, the nonionic polyalkoxylated surfactant present in the external aqueous phase has an HLB value greater than or equal to 10.

By way of example of nonionic polyalkoxylated surfactant suitable for use in the invention, the following surfactants, alone or in the form of mixtures, may be mentioned;
alkoxylated fatty alcohols
alkoxylated triglycerides
alkoxylated fatty acids
alkoxylated sorbitan esters
alkoxylated fatty amines
alkoxylated di(1-phenylethyl)phenols
alkoxylated tri(1-phenylethyl)phenols
alkoxylated alkylphenols.

The alkoxylated units are preferably ethoxylated units or a mixture of ethoxylated and propoxylated units.

The surfactant mentioned as being suitable for the preparation of the inverse emulsion may be repeated, except for the fact that the number of ethoxylated units and, if they are present, propoxylated units, should be adjusted according to the desired HLB value. Purely as an illustration, the number of ethoxylated and optionally propoxylated units is between 10 and 100.

As regards the polyalkoxylated nonionic amphiphilic polymer, the latter satisfies the Bancroft rule and its two conditions set out above, and comprises at least two blocks, one of them being hydrophilic, the other hydrophobic; at least one of the blocks comprising polyalkoxylated, more particularly polyethoxylated and/or polypropoxylated, units.

What was indicated above in the context of the description of the nonionic hydrophilic monomers, of the hydrophobic monomers which can be used for the preparation of amphiphilic block polymers entering into the composition of the inverse emulsion, and methods of synthesis, remains valid and will not be repeated here.

Purely as a guide, said polymers are obtained using in particular anionic ring opening polymerizations.

More particularly, said nonionic polyalkoxylated amphiphilic polymers are chosen from the polymers whose weight-average molar mass is less than or equal to 100 000 g/mol (measured by GPC, polyethylene glycol standard), preferably between 1 000 and 50 000 g/mol, preferably between 1 000 and 20 000 g/mol.

By way of examples of polymers of this type, there may be mentioned, inter alia, polyethylene glycol/polypropylene glycol/polyethylene glycol triblock polymers. Such polymers are well known and are in particular marketed under the trademarks Pluronic (marketed by BASF), Arlatone (marketed by ICI).

It should be noted that there will be no departure from the scope of the present invention on combining one or more surfactants with one or more amphiphilic polymers.

However, according to a preferred embodiment of the invention, the external aqueous phase comprises one or more amphiphilic polymers.

The content of nonionic polyalkoxylated surfactant and/or of nonionic polyalkoxylated amphiphilic polymer present in the external aqueous phase is more particularly between 1 and 10% by weight relative to the weight of the inverse emulsion. Preferably, the content of nonionic surfactant and/or of amphiphilic polymer is between 1 and 5% by weight relative to the weight of the inverse emulsion.

It should be noted that if the internal organic phase has a relatively high viscosity, for example of greater than or equal to 5 Pa·s (dynamic viscosity measured using Brookfield at 25° C., according to the NFT 76 102 standard of February 1972), it may be advantageous to add to the external aqueous phase at least one thermothickening polymer.

The thermothickening polymers have the specific feature of giving aqueous solutions whose viscosity increases when the temperature exceeds the temperature for thickening of the thermothickening polymer; the temperature above which the viscosity of the medium in which said polymer is present increases.

More particularly, these polymers are soluble in water at room temperature, and above the thickening temperature, part of the polymer becomes hydrophobic (heat-sensitive part): the polymer thus forms a physical network on a microscopic scale, which results on a macroscopic scale in an increase in viscosity.

According to an advantageous embodiment of the present invention, the thermothickening polymer used is chosen from polymers exhibiting a jump in viscosity between 25 and 80° C. such that the value of the $\log_{10}$(viscosity at 80° C.)/$\log_{10}$ (viscosity at 25° C.) ratio is at least equal to 1, preferably at least equal to 2.

The ratio is measured under the following conditions:
The polymer is first of all dissolved in water (dry extract of 4%).

The rheological profile is then measured in a forced stress flow mode, scanning the temperature between 20° C. and 80° C. The configuration used is the flat-cone geometry 4 cm/1 degree. The stress introduced into the program is chosen (in manual mode) such that the gradient at 25° C. is 10 s$^{-1}$. The parameter which was selected for characterizing the thermothickening power of the polymer, that is the $\log_{10}$(viscosity at 80° C.)/$\log_{10}$(viscosity at 25°) ratio, represents the jump in viscosity, expressed in decades, from 25 to 80° C. This parameter expresses in other words that the viscosity of the medium at 80° C. is greater than $10^n$ times the viscosity of the medium at 25° C.; with n integer between 0 and 5.

In addition to this characteristic, the thermothickening polymer is chosen such that the variation in viscosity is reversible.

Among the thermothickening polymers which can be used, there may be mentioned hydrophobic modified polysaccharides such as carboxymethyl celluloses, methyl celluloses, hydroxyethyl celluloses and hydroxypropyl celluloses.

In the case of this type of polymer, it may be advantageous to use them combined with at least one additional surfactant, chosen from nonionic or anionic surfactants.

Also suitable are synthetic polymers such as polymers based on N-isopropyl acrylamide, polymers based on N,N-dimethyl aminoethyl methacrylate.

Polymers with a comb structure consisting of a polymeric backbone segment on which are grafted at least two polymeric side segments, which are identical or different, for which either the polymeric backbone segment, or the polymeric side segments possess a lower critical solution temperature, such as LCST, of between 25 and 80°. Preferably, the polymeric side segments are heat-sensitive and are derived from polyalkoxylated polymers.

By way of examples of polymers of this type, there may be mentioned in particular polymers prepared from POE-POP-POE polymer triblocks and acrylic acid (respective molar percentages: 2.3%, 97.7%, direct grafting), polymers prepared from a macromonomer of triblocks POE-POP-POE and acrylic acid (respective mol %: 1.6%, 98.4%, copolymerization), polymers prepared from a macromonomer of triblocks POE-POP-POE and acrylic acid (respective mol %: 3%, 97%, copolymerization), polymers prepared from a macromonomer of triblocks POE-POP-POE and acrylic acid (respective mol %: 2%, 98%, copolymerization).

These polymers were the subject of French patent application FR 2 180 422, to which reference may be made for more information on polymers and their production.

The content of thermothickening polymer represents more particularly, when it is present, 0.2 to 10% by weight of the external aqueous phase. Preferably, the content of the polymer represents 1 to 5% by weight of the external aqueous phase.

The external aqueous phase comprises, moreover, at least one water-soluble or water-dispersible compound provided in a solid form in the presence of a water content of at most 10% by weight relative to the weight of said polymer and whose glass transition temperature is greater than 25° C., preferably greater than 50° C.

The expression water-soluble or water-dispersible compound denotes a compound which precipitates when it is in aqueous solution, at 25° C., with the nonionic polyalkoxylated surfactant and/or the nonionic amphiphilic polyalkoxylated polymer present in the external aqueous phase of the multiple emulsion; the total concentration of said polyalkoxylated surfactant/polyalkoxylated polymer being between 2 and 10% by weight and the concentration of compound corresponding to a content of between 30 and 85% by weight in the dried final granule (and according to the preferred variants which will be explicitly stated later, the concentration of compound corresponding to a content of between 30 and 70% by weight relative to the same reference, or between 50 and 85% by weight relative to the same reference).

More particularly, said water-soluble or water-dispersible compound is chosen from:
(i) at least one polymer obtained by polymerization
  of at least one monomer (I) which is an ethylenically unsaturated, linear or branched, aliphatic, cyclic or aromatic monocarboxylic or polycarboxylic acid, or anhydride, and
  of at least one monoethylenically or polyethylenically unsaturated, linear or branched hydrocarbon monomer (II), and/or
  of at least one monomer (III) which is a polyalkoxylated ester of ethylenically unsaturated carboxylic acid;
(ii) at least one polymer obtained from the polymerization of at least one monomer (I) which is an ethylenically unsaturated, linear or branched, aliphatic, cyclic or aromatic, monocarboxylic or polycarboxylic acid, or anhydride, and optionally comprising at least one saturated or unsaturated, aromatic or nonaromatic, hydrophobic $C_4$-$C_{30}$ hydrocarbon graft, optionally interrupted by one or more heteroatoms;
(iii) proteins and polypeptides of natural or synthetic origin, optionally comprising at least one saturated or unsaturated, aromatic or nonaromatic, hydrophobic $C_4$-$C_{30}$ hydrocarbon graft, optionally interrupted by one or more heteroatoms;
(iv) polysaccharides, preferably highly depolymerized, optionally containing at least one saturated or unsaturated, aromatic or nonaromatic, hydrophobic $C_4$-$C_{30}$ hydrocarbon graft, optionally interrupted by one or more heteroatoms;
(v) polyvinyl alcohol, polyvinylpyrrolidone.

According to a first variant of the invention, the water-soluble or water-dispersible compound is a polymer obtained from the polymerization:
  of at least one monomer (I) which is an ethylenically unsaturated, linear or branched, aliphatic, cyclic or aromatic monocarboxylic or polycarboxylic acid, or anhydride, and
  of at least one monoethylenically or polyethylenically unsaturated, linear or branched hydrocarbon monomer (II), and/or
  of at least one monomer (III) which is a polyalkoxylated ester of an ethylenically unsaturated carboxylic acid.

According to a particular embodiment of this first variant, there may be mentioned, first of all, polymers derived from the polymerization:
  of at least one monomer of formula (I):

(I)

in which formula the radicals $R^1$, $R'^1$, which are identical or different, represent a hydrogen atom a $C_1$-$C_{10}$ hydrocarbon radical optionally comprising a —COOH group, a —COOH group; and
  of at least one monomer of formula (II):

(II)

in which formula the radicals $R^2$, which are identical or different, represent a linear or branched $C_1$-$C_{10}$ hydrocarbon radical. More particularly, said radicals are alkyl or alkenyl radicals, it being possible for the latter to comprise one or more ethylenic unsaturations. Preferably, said radicals do not comprise heteroatoms.

According to a preferred embodiment of the invention, the monomer of formula (I) is such that one of the radicals $R^1$ is a hydrogen atom; the other radical $R^1$ represents a hydrogen atom, a —COOH group or a —$(CH_2)_n$—COOH group in which n is between 1 and 4, a $C_1$-$C_4$ alkyl radical; $R'^1$ represents a hydrogen atom, as a —$(CH_2)_m$—COOH group in which m is between 1 and 4, a $C_1$-$C_4$ alkyl radical.

Preferably, one of the radicals $R^1$ represents a hydrogen atom, the other radical $R^1$ represents a hydrogen atom, a —COOH or $(CH_2)$—COOH group, a methyl radical, and $R'^1$ represents a hydrogen atom, a —$CH_2COOH$ group or a methyl radical.

According to a more particular embodiment, the monomer of formula (I) is chosen from acrylic, methacrylic, citraconic, maleic, fumaric, itaconic and crotonic acids or anhydrides.

As regards the monomer of formula (II), the latter may in particular be chosen from ethylene, propylene, 1-butene, isobutylene, n-1-pentene, 2-methyl-1-butene, n-1-hexene, 2-methyl-1-pentene, 4-methyl-1-pentene, 2-ethyl-1-butene, diisobutylene (or 2,4,4-trimethyl-1-pentene), 2-methyl-3,3-dimethyl-1-pentene.

According to an advantageous embodiment of the invention, the monomer (I)/monomer (II) molar ratio is between 30/70 and 70/30.

Preferably, the copolymer of formula (i) is derived from the polymerization of maleic anhydride and 2,4,4-trimethyl-1-pentene.

It is specified that the polymer (i) is obtained more particularly by carrying out a free-radical polymerization of the monomers (I) and (II).

These compounds are well known to persons skilled in the art. As a polymer of this type, there may be mentioned that marketed under the name Geropon® T36 (maleic anhydride/diisobutylene), marketed by Rhodia Chimie, and Sokalan® CP9 (maleic anhydride/olefin) marketed by BASF.

A second particular embodiment of this first variant consists in using a polymer (I) obtained by polymerization of at least one monomer of formula (I) described above, with at least one monomer of formula (III):

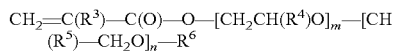

in which formula:
$R^3$ is a hydrogen atom or a methyl radical,
$R^4$ and $R^5$, which are identical or different, represent a hydrogen atom or an alkyl radical containing from 1 to 4 carbon atoms,
$R^6$ is an alkyl, aryl, alkylaryl or arylalkyl radical containing from 1 to 30, preferably from 8 to 30 carbon atoms,
n is between 2 and 100, preferably between 6 and 100 and m is between 0 and 50, provided that n is greater than or equal to m and their sum is between 2 and 100, preferably between 6 and 100.

Preferably, monomers of formula (III) are used for which $R^6$ is an alkyl radical containing from 8 to 30 carbon atoms, a phenyl radical substituted with one to three 1-phenylethyl groups, an alkylphenyl radical in which the alkyl radical contains from 8 to 16 carbon atoms.

Among the monomers of this type, which can be used, there may be mentioned those described in patents EP 705 854, U.S. Pat. No. 4,138,381 or U.S. Pat. No. 4,384,096.

The polymer obtained by reacting the monomers (I) and (III) is preferably obtained by free-radical polymerization.

It should be noted that there will be no departure from the scope of the present invention on using a polymer (i) comprising the three monomers which have just been described.

As a guide, the weight-average molecular mass of polymers (i) is more particularly less than 20 000 g/mol; absolute weight-average molecular masses determined by size exclusion chromatography coupled with the MALLS method.

It is specified that the molecular mass of the polymer and the respective proportions of the monomers (I) and (II) and/or (III) are such that the resulting polymer is water-soluble or water-dispersible for the purposes of the present invention.

A second variant of the present invention consists of the use, as a water-soluble or water-dispersible compound, of at least one polymer obtained from the polymerization of at least one monomer of formula (I) as defined above and containing, in addition, optionally at least one saturated or unsaturated, aromatic or nonaromatic hydrophobic $C_4$-$C_{30}$ hydrocarbon graft, optionally interrupted by one or more heteroatoms.

All that has been indicated above in relation to the monomer of formula (I), general and preferred formulae, remains applicable in the case of the polymer (ii) and will therefore not be repeated here.

It should be noted that this polymer is preferably obtained using free-radical polymerization.

Moreover, the hydrophobic graft is chosen from aliphatic, cyclic, aromatic, alkylaromatic and arylaliphatic radicals comprising 4 to 30 carbon atoms, and which may be interrupted by one or more heteroatoms, preferably oxygen.

It should be noted that the grafts are linked to the backbone of the polymer by means of ester and/or amide groups.

Such graft polymers are obtained using methods known to persons skilled in the art consisting, in a first instance, in polymerizing, preferably by the free-radical route, the monomer(s) (I), and then in reacting part of the free carboxyl functional groups with reagents chosen in particular from hexyl, heptyl, lauryl and behenyl amines or alcohols, which are optionally ethoxylated and/or propoxylated, mono-, di- or tristyrylphenols which are optionally ethoxylated and/or propoxylated.

As a guide, the weight-average molecular mass of the polymers (ii) is more particularly less than 20 000 g/mol; absolute weight-average molecular masses, determined by size exclusion chromatography coupled with the MALLS method.

However, the molecular mass and the respective proportions of the monomer(s) (I) and of the hydrophobic grafts, if they are present, is such that the resulting polymer is water-soluble or water-dispersible for the purposes of the present invention.

The polymers (i) and (ii) may, in addition, comprise units corresponding to monoethylenically saturated nonionic monomers (IV) other than the monomers (II).

Among the monoethylenically unsaturated nonionic monomers (IV), there may be mentioned:
vinylaromatic monomers such as styrene, vinyltoluene,
$C_1$-$C_{20}$ alkyl esters of acids which are α-β-ethylenically unsaturated, such as acrylates or methacrylates of methyl, ethyl or butyl,
vinyl or allyl esters of acids which are α-β-ethylenically unsaturated, such as acetates or propionates of vinyl or allyl,
vinyl or vinylidene halides such as vinyl or vinylidene chloride,
⊕-β-ethylenically unsaturated nitriles such as acrylonitrile,
hydroxyalkyl esters of acids which are α-β-ethylenically unsaturated, such as hydroxyethyl or hydroxypropyl acrylates or methacrylates,
α-β-ethylenically unsaturated amides such as acrylamide, methacrylamide.

If such monomers are present, the polymerization occurs in their presence.

A third variant of the present invention consists in using, as water-soluble or water-dispersible compound, at least one protein, or at least one polypeptide of natural or synthetic origin, optionally containing at least one saturated or unsaturated, aromatic or nonaromatic, hydrophobic $C_4$-$C_{30}$ hydrocarbon graft, optionally interrupted by one or more heteroatoms.

The peptide polymers of natural or synthetic origin are polymers derived from the polycondensation of amino acids, in particular of aspartic and glutamic acid or precursors of diamino diacids, and hydrolysis. These polymers may be either polymers derived from aspartic or glutamic acid, polymers derived from aspartic acid and glutamic acid in any proportions, or copolymers derived from aspartic and/or glutamic acid and other amino acids. Among the polymerizable amino acids, there may be mentioned, inter alia, glycine, alanine, leucine, isoleucine, phenylalanine, methionine, histidine, proline, lysine, serine, threonine, cysteine, and the like.

Among the polypeptides of natural origin, there may be mentioned water-soluble or water-dispersible proteins of plant or animal origin. The proteins of plant origin are preferably protein hydrolysates. Their degree of hydrolysis is more particularly less than or equal to 40%.

Among the proteins of plant origin, there may be mentioned, as a guide, proteins obtained from high-protein seeds, in particular those from peas, field beans, lupine, haricot beans and lentil; proteins obtained from seeds of cereals, in particular those of wheat, barley, rye, corn, rice, oats, millet; proteins obtained from oil-bearing seeds, in particular those of soybean, peanut, sunflower, rape and coconut; proteins obtained from leaves, in particular lucerne and nettle; proteins obtained from plant organs and underground storage organs, in particular those of potato and beet.

Among the proteins of animal origin, there may be mentioned, for example, muscle proteins, in particular stromal proteins, gelatin, proteins obtained from milk, in particular casein, lactoglobulin; and fish proteins.

The proteins of plant origin, and more particularly the proteins obtained from soybean and wheat are preferred.

What was indicated above in relation to the nature of the hydrophobic graft remains valid and will not be repeated here.

It should be noted that the hydrophobic grafts may be linked to the polypeptide by means of amide, ester, urea, urethane, isocyanate or amino bonds.

The graft polymers are obtained by reacting part of the free amine or acid functional groups with compounds which make it possible to create the abovementioned bonds.

The preferred compounds exhibit a degree of polymerization which is low. More particularly, by way of illustration, the weight-average molecular mass is less than 20 000 g/mol; absolute weight-average molecular masses, determined by size exclusion chromatography coupled with the MALLS method.

It is specified that the molecular mass of the polymer, and the proportion of graft relative to the polypeptide, when it is present, are such that the resulting polymer is water-soluble or water-dispersible for the purposes of the present invention.

According to a fourth variant of the present invention, the water-soluble or water-dispersible compound is chosen from polysaccharides optionally containing a saturated or unsaturated, aromatic or nonaromatic, hydrophobic $C_4$-$C_{30}$ hydrocarbon graft, optionally interrupted by one or more heteroatoms.

By way of nonlimiting example of suitable polysaccharides, there may be mentioned, inter alia, starch, modified starch, alginates, hydroxyalkyl celluloses or their derivatives.

According to a preferred embodiment of the invention, the water-soluble or water-dispersible compound is chosen from highly depolymerized polysaccharides optionally containing a saturated or unsaturated, aromatic or nonaromatic, hydrophobic $C_4$-$C_{30}$ hydrocarbon graft, optionally interrupted by one or more heteroatoms.

Such compounds are in particular described in the book by P. ARNAUD entitled "cours de chimie organique", GAUTHIER-VILLARS publishers, 1987.

Among such compounds, there may be mentioned those obtained from dextran, starch, maltdextrin, xanthan gum and galactomannans such guar or carob.

These highly depolymerized polysaccharides preferably have a melting point greater than 100° C. and a water-solubility of between 50 and 500 g/l, at 25° C.

On the subject of the hydrophobic grafts, reference may be made to what was indicated above.

It should be noted that the hydrophobic grafts may be linked to the polysaccharide by means of ester, amide, urea, urethane, isocyanate or amino bonds.

The graft polymers are obtained by reacting part of the free alcohol or acid functional groups with compounds which make it possible to create the abovementioned bonds.

More particularly, by way of illustration, the weight-average molecular mass of these highly depolymerized polysaccharides is less than 20 000 g/mol; absolute weight-average molecular masses determined by size exclusion chromatography coupled with the MALLS method.

However, it is specified that the molecular mass of the polysaccharide, whether it is highly depolymerized or not, and the proportion of graft, if it is present, relative to said polysaccharide are such that the resulting polymer is either water-soluble or water-dispersible for the purpose of the present invention.

According to a final variant of the invention, the water-soluble or water-dispersible compound is a polyvinyl alcohol, polyvinylpyrrolidone.

It should be noted that the polyvinyl alcohol may be partially or completely in hydrolyzed form, as long as it is water-soluble or water-dispersible for the purposes of the present invention.

Of course, it is completely possible to envisage using these various types of water-soluble or water-dispersible compounds in combination.

The content of water-soluble or water-dispersible compound in the external aqueous phase is moreover such that the content of this compound in the final granule is more particularly between 30 and 85% by weight relative to the weight of said granule.

It should be noted that in the particular case where the water-soluble or water-dispersible compound is chosen from proteins, polyvinyl alcohol, polyvinylpyrrolidone or from polysaccharides, the content of this compound in the final granule is more particularly between 50 and 85% by weight relative to the weight of said granule.

In addition, in the case where the water-soluble or water-dispersible compound is chosen from the variants (i), (ii), the highly depolymerized polypeptides and polysaccharides, the content of this compound in the final granule is very advantageously between 30 and 70% by weight relative to the weight of said granule.

Furthermore, the inverse emulsion/external aqueous phase weight ratio is usually between 30/70 and 90/10, preferably between 50/50 and 90/10.

In order to equilibrate the osmotic pressures of the external aqueous phase and of the internal aqueous phase, it is possible to add to the external aqueous phase at least one additive chosen from salts such as alkali or alkaline-earth metal halides (such as sodium chloride, calcium chloride), at least one alkali or alkaline-earth metal sulfate (such as calcium sulfate); or chosen from sugars (glucose for example), or from polysaccharides (in particular dextran) or mixtures thereof.

The concentrations of additive (salt, of sugar and/or of polysaccharide) are such that the osmotic pressures of the external and internal aqueous phases are in equilibrium.

Furthermore, depending on the application for which the granule according to the invention is intended, or depending on the nature of the active substance, it may be advantageous to adjust the pH of the external aqueous phase by adding a base (sodium hydroxide, potassium hydroxide) or an acid (hydrochloric acid), once the multiple emulsion has been obtained.

By way of illustration, the usual pH range for the external aqueous phase is between 3 and 8, preferably between 5 and 8.

According to an advantageous variant of the present invention, the aqueous phase of the emulsion may comprise at least one thickening polymer. This polymer has the effect of avoiding creaming and/or sedimentation of the final emulsion.

By way of illustration, it is possible to use thickening polymers extracted from plants and optionally modified, such as carrageenans, alginates, carboxymethyl celluloses, methyl celluloses, hydroxypropyl celluloses, hydroxyethyl celluloses, gellans.

It is likewise possible to use thickening polymers of the polysaccharide type of animal, plant or bacterial origin; there may be mentioned by way of nonlimiting example xanthan gum, guar and derivatives (such as hydroxypropyl guar for example), polydextroses, or combinations thereof.

When it is present, the content of thickening polymer is more particularly between 0.1 and 2% by weight relative to the external aqueous phase, preferably between 0.1 and 0.5% by weight relative to the external aqueous phase. It should be specified that in this concentration range, the thickening polymer is soluble in the aqueous phase.

There will be no departure from the scope of the present invention on mixing several multiple emulsions, as long as the external aqueous phases of the mixed emulsions are compatible.

According to one variant of the present invention, the external aqueous phase may comprise a dispersed organic phase and/or a dispersed solid.

All that has been indicated above relating to the hydrophobic active substance optionally present in the internal organic phase remains valid and will not be again detailed now.

It should be noted that these active substances may be used in the presence of conventional additives in the relevant field of application.

In the case where such an external organic phase is present, it represents more particularly 1 to 50% by weight of the external aqueous phase, preferably 5 to 25% by weight of the external aqueous phase.

In addition, it is preferable that the size of the droplets of the external organic phase are at most of the same order of magnitude as that of the inverse emulsion dispersed in the external aqueous phase.

As for the possibility of using a solid dispersed in the external aqueous phase, all solids used in the various applications mentioned above may be suitable. Preferably, the size of this dispersed solid is close to or lower than that of the droplets of the inverse emulsion.

In the case where the dispersed solid is present, its content represents more particularly 1 to 50% by weight of the external aqueous phase, preferably 5 to 25% by weight.

The preparation of the multiple emulsion may be carried out according to any known method.

By way of example of preparation of the multiple emulsion, in the case where no thermothickening polymer is used, the procedure may be carried out by mixing the water, the nonionic surfactant and/or the nonionic amphiphilic polymer, and optionally the additive. Preferably, the water and the surfactant and/or the amphiphilic polymer are first of all mixed, with stirring; the water-soluble or water-dispersible compound is then added.

This operation usually takes place at a temperature greater than the melting point of the compound used as internal organic phase. Preferably, this temperature is between 20 and 80° C.

The external aqueous phase may be optionally allowed to stand for 1 to 12 hours at room temperature.

The actual multiple emulsion is then prepared by adding the inverse emulsion to the external aqueous phase.

This operation takes place with stirring, the inverse emulsion being initially slowly added.

The stirring may be carried out by means of a frame-type blade. Typically, the stirring rate is relatively slow, of the order of 400 rpm.

In the case where a thermothickening polymer is used, several variants may be envisaged.

For example, the external aqueous phase is prepared by mixing its various constituent components. More particularly, the water, the surfactant and/or the amphiphilic polymer are mixed. The temperature of the mixture is then increased to a temperature greater than or equal to the thickening temperature of the thermothickening polymer. It should be noted that the temperature is advantageously greater than or equal to the melting point of the compound used as internal organic phase.

Next, the inverse emulsion is added to the external aqueous phase thus obtained. This operation takes place at a temperature of greater than or equal to the thickening temperature of the thermothickening polymer.

Once the multiple emulsion has been obtained, the whole is heated to a temperature less than the thickening temperature of the thermothickening polymer and the water-soluble or water-dispersible compound is then added, with stirring.

The stirring conditions are of the same type as the preceding variant, namely a slow stirring, of the order of 400 revolutions/minute.

According to another possibility, the combination of all the constituent components of the external aqueous phase are mixed. Preferably, the surfactant and/or amphiphilic polymer, optionally the additive, the thermothickening polymer and then the water-soluble or water-dispersible compound are added to the water, with stirring.

Next, the temperature of the mixture is adjusted such that it is greater than or equal to the thickening temperature of the thermothickening polymer and/or than the melting point of the compound used as organic phase of the inverse emulsion. The inverse emulsion is then added to the external aqueous phase at the appropriate temperature.

The stirring is preferably slow, of the order of 400 to 700 revolutions/minute.

In the case where the external aqueous phase comprises a dispersed external organic phase, the multiple emulsion is preferably obtained by dispersing the inverse emulsion in the external aqueous phase. The direct emulsion, composed of the external organic phase dispersed in the same external aqueous phase, is then added. Quite obviously, the quantities of external aqueous phase introduced with the inverse and direct emulsions are such that the proportions by weight of each of the phases will satisfy the conditions explicitly stated above for the multiple emulsion.

The direct emulsion is obtained according to any known method, by mixing, with stirring, the two phases: the external organic phase comprising the hydrophobic active substance and the external aqueous phase comprising the surfactant and/or the amphiphilic polymer, the water-soluble or water-dispersible compound and optionally the thermothickening polymer.

In the case where the external aqueous phase comprises a dispersed solid, the production of the multiple emulsion may be carried out as indicated in the first case, and then said dispersed solid is added to the external aqueous phase.

The average size of the droplets of the multiple emulsion advantageously vary between 5 and 100 µm, more particularly between 5 and 50 µm, advantageously between 5 and 15

μm. They are measured by means of a Horiba granulometer, and correspond to the median diameter by volume (d50) which represents the diameter of the particle equal to 50% of the cumulative distribution.

The multiple emulsion is then dried so as to obtain the granules according to the invention.

The drying operation may be carried out by any means known to persons skilled in the art.

More particularly, the drying operation is performed under conditions such that the external aqueous phase is removed.

Preferably, the drying is carried out such that at least 90% by weight of the external aqueous phase is removed, preferably between 90 and 95% by weight.

By carrying out the drying under such conditions, the dried granules according to the present invention comprise an internal water content of between 10 and 50% by weight of the granule, preferably between 20 and 30% by weight of the granule.

Thus, according to a first embodiment of the invention, it is possible to envisage drying in an oven. Preferably, this drying is performed in a thin layer.

Usually, the drying temperature is less than or equal to 100° C. More particularly, temperatures between 50 and 90° C. are suitable for carrying out this method.

According to another preferred embodiment of the invention, a so-called rapid method for drying the multiple emulsion is used.

Suitable in this regard is spray-drying, or drying using Duprat® drums, or alternatively freeze-drying (freezing-sublimation).

These modes of drying such as in particular spray-drying, are particularly recommended because they make it possible to preserve the multiple emulsion as it is and to obtain granules directly.

The spray-drying may be carried out in the customary manner in any known apparatus, such as for example a spray-drying tower combining spraying carried out using a nozzle or a turbine with a stream of hot gas.

The outlet temperature of the spray-drying gases is preferably between 55 and 75° C. These temperatures are given as a guide, and depend on the thermal stability of the various components. Furthermore it is defined according to the final water content desired in the granule.

In the case of operations for drying the multiple emulsion which are carried out by means of a Duprat® drum, or by any means which makes it possible to rapidly obtain a dry film which is separated from the drying support by a scraping operation for example, granules are obtained which may be optionally ground. If necessary, these granules may be the subject of subsequent processing, such as an agglomeration stage, so as to obtain agglomerated granules.

It should be noted that additives, such as anticaking agents, may be incorporated into the granules during this second drying stage.

It is likewise possible, by way of example, to use a filler chosen in particular from calcium carbonate, barium sulfate, kaolin, silica, bentonite, titanium oxide, talc, hydrated alumina and calcium sulfoaluminate.

The additives may be introduced before drying the multiple emulsion, as may be in particular the case for fillers. They may also be co-dried with the multiple emulsion, as is in particular the case for anticaking agents.

Advantageously, the average size of the granules obtained directly after drying is between 100 μm and a few millimeters, preferably between 100 and 800 μm. The average size of the granules is measured with a Sympatec apparatus and corresponds to the median diameter by volume (d50) which represents the diameter of the particle equal to 50% of the cumulative distribution.

The granules according to the invention, when they are dispersed in an aqueous phase, make it possible to obtain a multiple emulsion again.

The granules according to the invention may be stored and transported without any difficulty.

A concrete but nonlimiting example of the invention will now be presented.

EXAMPLE

1 /Inverse Emulsion

Composition of the Inverse Emulsion:

*30% of aqueous phase:
  14% of lactic acid (% by weight of a 0.1 M solution expressed relative to the weight of the aqueous phase)
  86% of NaCl (% by weight of 0.1 M solution expressed relative to the weight of the aqueous phase)

*70% of oily phase (soybean oil and surfactant) comprising 5% of surfactant (Arlacel P135; ICI-Uniquema (*); % expressed by weight relative to the weight of aqueous phase).

(*) Arlacel P 135: polyhydroxystearate-PEG-polyhydroxystearate; HLB=5-6; Mw≈5 000 g/mol)

Preparation of the Inverse Emulsion 300 g of inverse emulsion are prepared which comprise 210 g of internal organic phase and 90 g of internal aqueous phase.

On the one hand, 12.6 g of a 0.1 M lactic acid solution are mixed with 77.4 g of a 0.1 M NaCl solution.

On the other hand, 4.5 g of Arlacel P135 are mixed with 205.5 g of soybean oil. Prior to the mixing, the soybean oil and the Arlacel were placed in an oven at 75° C.

The internal aqueous phase is then added to the internal organic phase, with stirring using Ultraturrax at 9 500 rpm. The mixing is carried out at 75° C. Refining is then carried out at 9 500 rpm for 8 minutes.

2 /Multiple Emulsion

Composition of the Multiple Emulsion:

*65% of inverse emulsion

*35% of dry extract in an external aqueous phase containing:
  2% of Arlatone F127G (**) (ICI-Uniquema; % by weight expressed relative to the weight of the inverse emulsion);
  51.8% of Geropon T36 (***) (Rhodia Chimie; % by weight of the solution of Geropon T 36; expressed relative to the weight of the inverse emulsion);
  47.2% of a 2 N hydrochloric acid solution (% by weight expressed relative to the weight of Geropon T36)

(**) Arlatone F127G: $HO(CH_2CH_2O)_x(OCH(CH_3)CH_2O)_y(CH_2CH_2O)_zH$ with verification of the following inequality: $82 < x+z < 90$ and the polymer comprises 7 PO units per 1 mol of product).

(***) Geropon T36: Maleic anhydride/diisobutylene copolymer; Mw=5 000 g/mol.

Preparation of the Multiple Emulsion

Preparation of the External Aqueous Phase:

In a 2 liter beaker, 6 g of Arlatone F127G are dissolved in 200 g of water, with stirring using a frame-type blade at 300 rpm for 30 minutes.

622.15 g of Geropon T36 solution (solution in water at 25% by weight) are then added to the Arlatone solution.

Preparation of the Multiple Emulsion:

The 300 g of the inverse emulsion obtained in point 1/ are introduced, with stirring using a frame-type blade at 300 rpm, dropwise and then gently, into the external aqueous phase, at room temperature.

Immediately after the introduction of the inverse emulsion, 73.8 g of the HCl solution (2 N) are added all at once, with stirring at 400 rpm, at room temperature.

The stirring is maintained for 1 hour at 400 rpm.

The pH of the external aqueous phase of the multiple emulsion thus obtained is 7.5.

The average size of the droplets of the multiple emulsion is about 10 to 15 μm (Horiba granulometer).

3 /Drying of the Multiple Emulsion

The multiple emulsion is spray-dried.

The drops of multiple emulsion produced traverse a descending tangential stream of hot air and form, on drying, granules which are recovered at the bottom part.

The spray-drying conditions are the following:

T inlet: 110° C./T outlet: 60° C.

P for spraying on a bifluid nozzle: 2 bar absolute

V dried multiple emulsion: 600 ml/M dry emulsion:≈132 g

4 /Test of Redispersion of the Granules

Using a spatula, a few milligrams of dry emulsion are redispersed in distilled water.

The redispersion is immediate and a multiple emulsion is again obtained in which the size of the droplets is between 10 and 15 μm (according to observations by optical microscopy and using a Horiba granulometer).

The invention claimed is:

1. A granule made by the process of drying an inverse emulsion, dispersed in an external aqueous phase, wherein:
    (a) the inverse emulsion comprises an internal aqueous phase comprising at least one hydrophilic active substance, dispersed in an internal organic phase, said inverse emulsion comprising at least one nonionic surfactant, at least one amphiphilic block polymer, or at least one cationic surfactant; and
    (b) the external aqueous phase comprises:
    at least one polyalkoxylated nonionic surfactant or at least one polyalkoxylated amphiphilic nonionic polymer, and
    at least one water-soluble or water-dispersible polymer,
        wherein said at least one water-soluble or water-dispersible polymer:
            is a solid in the presence of a water content of at most 10% by weight relative to the weight of said at least one water-soluble or water-dispersible polymer, and
            has a glass transition temperature of greater than 25° C.

2. The granule as claimed in claim 1, wherein the nonionic surfactant and the amphiphilic block polymer, when mixed with the internal organic phase at a concentration ranging from 0.1 to 10% by weight of said phase at 25° C., are soluble in the internal organic phase in at least part of the concentration range; and further wherein the nonionic surfactant and the amphiphilic block polymer, when mixed with the internal aqueous phase, at a concentration ranging from 0.1 to 10% by weight of said phase at 25° C., are dispersible in the internal aqueous phase in at least part of the concentration range.

3. The granule as claimed in claim 1, wherein the nonionic surfactant, the amphiphilic block polymer, or the cationic surfactant is present in a quantity representing 2 to 10% by weight of the internal aqueous phase.

4. The granule as claimed in claim 1, wherein the inverse emulsion has an aqueous phase/organic phase weight ratio between 10/90 and 90/10.

5. The granule as claimed in claim 4, wherein the aqueous phase/organic phase weight ratio, is between 30/70 and 80/20.

6. The granule as claimed in claim 1, wherein the internal aqueous phase further comprises an additive comprising an alkali metal halide, an alkaline-earth metal halide, an alkali metal sulfate, an alkaline-earth metal sulfate, a sugars, a polysaccharide, or mixtures thereof.

7. The granule as claimed in claim 6, wherein the halide or sulfate additive has a concentration in the internal aqueous phase of between 0.05 and 1 mol/l, and the concentration of sugar or polysaccharide is such that the osmotic pressure of the internal aqueous phase comprising the sugar or the polysaccharide corresponds to the osmotic pressure of an internal aqueous phase comprising 0.05 to 1 mol/l of salt.

8. The granule as claimed in claim 1, wherein the internal organic phase further comprises at least one hydrophobic active substance, compatible with the hydrophilic active substance present in the internal aqueous phase.

9. The granule as claimed in claim 1, wherein the at least one polyalkoxylated nonionic surfactant and at least one polyalkoxylated amphiphilic nonionic polymer, when mixed with the external aqueous phase at a concentration ranging from 0.1 to 10% by weight of said phase at 25° C., are soluble in the external aqueous phase in at least part of the concentration range; and further wherein the at least one polyalkoxylated nonionic surfactant or at least one polyalkoxylated amphiphilic nonionic polymer, when mixed with the internal organic phase, at a concentration ranging from 0.1 to 10% by weight of said phase at 25° C., are dispersible in the internal organic phase in at least part of the concentration range.

10. The granule as claimed in claim 1, wherein the external aqueous phase further comprises at least one thermothickening polymer.

11. The granule as claimed in claim 10, wherein the thermothickening polymer is a polymer exhibiting a jump in viscosity between 25 and 80° C. such that the value of the $\log_{10}$(viscosity at 80° C.)/$\log_{10}$(viscosity at 25° C.) ratio is at least equal to 1, or a polymer having a reversible variation of viscosity.

12. The granule as claimed in claim 10, wherein the thermothickening polymer is present in a content of between 0.2 and 10% by weight of the external aqueous phase.

13. The granule as claimed in claim 1, wherein the water-soluble or water-dispersible polymer comprises:
(i) at least one polymer obtained by polymerization
of at least one monomer (I) which is an ethylenically unsaturated, linear or branched, aliphatic, cyclic or aromatic monocarboxylic or polycarboxylic acid, or anhydride, and
of at least one monoethylenically or polyethylenically unsaturated, linear or branched hydrocarbon monomer, or
of at least one monomer (III) which is a polyalkoxylated ester of ethylenically unsaturated carboxylic acid;
(ii) at least one polymer obtained from the polymerization of at least one monomer (I) which is an ethylenically unsaturated, linear or branched, aliphatic, cyclic or aromatic, monocarboxylic or polycarboxylic acid, or anhydride, and optionally comprising at least one saturated or unsaturated, aromatic or nonaromatic, hydrophobic $C_4$-$C_{30}$ hydrocarbon graft, optionally interrupted by one or more heteroatoms;
(iii) proteins and polypeptides of natural or synthetic origin, optionally comprising at least one saturated or unsaturated, aromatic or nonaromatic, hydrophobic $C_4$-$C_{30}$ hydrocarbon graft, optionally interrupted by one or more heteroatoms;
(iv) polysaccharides, optionally containing at least one saturated or unsaturated, aromatic or nonaromatic, hydrophobic $C_4$-$C_{30}$ hydrocarbon graft, optionally interrupted by one or more heteroatoms; or
(v) polyvinyl alcohol, polyvinylpyrrolidone.

14. The granule as claimed in claim 1, wherein the water-soluble or water-dispersible polymer present in the external aqueous phase is a polymer (i) obtained from the polymerization
of at least one monomer of formula (I):

$$(R^1)(R^1)—C=C(R'^1)—COOH \qquad (I)$$

in which formula the radicals $R^1$, $R^1$, which are identical or different, represent a hydrogen atom, a $C_1$-$C_{10}$ hydrocarbon radical optionally comprising a —COOH group, a —COOH group; and
of at least one monomer of formula (II):

$$(R^2)(R^2)—C=CH_2 \qquad (II)$$

wherein the radicals $R^2$, which are identical or different, represent a linear or branched $C_1$-$C_{10}$ hydrocarbon radical; and/or
of at least one monomer of formula (III):

$$CH_2=C(R^3)—C(O)—O—[CH_2CH(R^4)O]_m—[CH(R^5)—CH_2O]_n—R^6$$

wherein:
$R^3$ is a hydrogen atom or a methyl radical,
$R^4$ and $R^5$, which are identical or different, represent a hydrogen atom or an alkyl radical containing from 1 to 4 carbon atoms,
$R^6$ is an alkyl, aryl, alkylaryl or arylalkyl radical containing from 1 to 30,
n is between 2 and 100, and m is between 0 and 50, provided that n is greater than or equal to m and their sum is between 2 and 100.

15. The granule as claimed in claim 14, wherein the monomer (I) of the polymer (i) is a monocarboxylic or polycarboxylic acid, or a carboxylic anhydride, is such that one of the radicals $R^1$ is a hydrogen atom; the other radical $R^1$ represents a hydrogen atom, a —COOH group or a —$(CH_2)_n$—COOH group, wherein n is between 1 and 4 a $C_1$-$C_4$ alkyl radical; $R'^1$ represents a hydrogen atom, as a —$(CH_2)_m$—COOH group in which m is between 1 and 4, a $C_1$-$C_4$ alkyl radical.

16. The granule as claimed in claim 14, wherein the monomer (I) of the polymer (i) is acrylic, methacrylic, citraconic, maleic, fumaric, itaconic, crotonic acids or anhydrides.

17. The granule as claimed in claim 14, wherein the monomer (II) is ethylene, propylene, 1-butene, isobutylene, n-1-pentene, 2-methyl-1-butene, n-1-hexene, 2-methyl-1-pentene, 4-methyl-1-pentene, 2-ethyl-1-butene, diisobutylene (or 2,4,4-trimethyl-1-pentene), or 2-methyl-3,3-dimethyl-1-pentene.

18. The granule as claimed in claim 14, wherein the group $R^6$ of the monomer (III) is an alkyl radical containing from 8 to 30 carbon atoms, a phenyl radical substituted with one to three 1-phenylethyl groups, or an alkyiphenyl radical, whose alkyl radical contains from 8 to 16 carbon atoms.

19. The granule as claimed in claim 13, wherein the hydrophobic graft is a, cyclic, aromatic, alkylaromatic or arylaliphatic radical comprising 4 to 30 carbon atoms, optionally interrupted by one or more heteroatoms.

20. The granule as claimed in claim 14, wherein the polymer (i) is obtained from the polymerization of maleic anhydride and 2,4,4-trimetbyl-1-pentene.

21. The granule as claimed in claim 13, wherein the polypeptides (iii) comprise polymers derived from at least aspartic acid or glutamic acid.

22. The granule as claimed in claim 13, wherein the polysaccharides (iv) comprise highly depolymerized compounds obtained from dextran, starch, maltodextrin, xanthan gum, or galactomannans.

23. The granule as claimed in claim 1, wherein the amount of the nonionic polyalkoxylated surfactant or the nonionic amphiphilic polyalkoxylated polymer in the external aqueous phase ranges from 1 to 10% by weight relative to the weight of the inverse emulsion.

24. The granule as claimed in claim 1, wherein the amount of the water-soluble or water-dispersible polymer in the external aqueous phase is such that the amount of said polymer in the final granule ranges from 30 to 85% by weight relative to the weight of said granule.

25. The granule as claimed in claim 1, wherein the weight ratio of inverse emulsion to external aqueous phase ranges from 30/70 to 90/10.

26. The granule as claimed in claim 1, wherein the osmotic pressures of the external aqueous phase and the internal aqueous phase are equilibrated by adding to the external aqueous phase, one additive comprising an alkali metal halide, an alkaline-earth metal halide, an alkali metal sulfate, an alkaline-earth metal sulfate, a sugar, a polysaccharide, or mixtures thereof.

27. The granule as claimed in claim 1, wherein the external aqueous phase further comprises a dispersed external organic phase or a dispersed solid.

28. The granule as claimed in claim 27, wherein the dispersed external organic phase represents 1 to 50% by weight of the external aqueous phase.

29. The granule as claimed in claim 27, wherein the dispersed solid represents 1 to 50% by weight of the external aqueous phase.

30. The granule as claimed in claim 1, wherein the granule has a water content of between 10 and 50% by weight of the granule.

31. The granule as claimed in claim 1, wherein said drying is spray-drying, or freeze-drying.

* * * * *

UNITED STATES PATENT AND TRADEMARK OFFICE
CERTIFICATE OF CORRECTION

PATENT NO. : 7,589,144 B2
APPLICATION NO. : 11/490339
DATED : September 15, 2009
INVENTOR(S) : Lannibois-Drean et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 331 days.

Signed and Sealed this

Twenty-first Day of September, 2010

David J. Kappos
*Director of the United States Patent and Trademark Office*